United States Patent
Burstein et al.

(10) Patent No.: US 6,368,354 B2
(45) Date of Patent: *Apr. 9, 2002

(54) ACETABULAR BEARING ASSEMBLY FOR TOTAL HIP JOINTS

(75) Inventors: Albert Burstein, Sarasota; C. Michael Mauldin, Lake City; Gary J. Miller, Gainesville, all of FL (US)

(73) Assignee: Exactech, Inc., Gainesville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/414,431

(22) Filed: Oct. 7, 1999

(51) Int. Cl.$^7$ .................................................. A61F 2/32
(52) U.S. Cl. .................................................. 623/22.28
(58) Field of Search ......................... 623/22.21, 22.23, 623/22.24, 22.27, 22.28

(56) References Cited

U.S. PATENT DOCUMENTS

| | | | |
|---|---|---|---|
| 3,982,281 A | * 9/1976 | Giliberty ................. | 623/22.24 |
| 4,479,271 A | * 10/1984 | Bolesky et al. .......... | 623/20.17 |
| 4,778,474 A | 10/1988 | Homsy | |
| 4,846,840 A | 7/1989 | Leclercq et al. | |
| 4,883,488 A | * 11/1989 | Bloebaum et al. ....... | 623/20.29 |
| 4,892,551 A | 1/1990 | Haber | |
| 4,969,910 A | * 11/1990 | Frey et al. ............... | 623/22.29 |
| 5,080,674 A | * 1/1992 | Jacobs et al. ............ | 623/20.17 |
| 5,080,677 A | * 1/1992 | Shelly ..................... | 623/22.24 |
| 5,326,354 A | 7/1994 | Kwarteng | |
| 5,480,448 A | 1/1996 | Mikhail | |
| 5,549,695 A | 8/1996 | Spotorno et al. | |
| 5,645,594 A | 7/1997 | Devanathan et al. | |
| 5,658,338 A | 8/1997 | Tullos et al. | |
| 5,658,345 A | 8/1997 | Willi | |
| 5,735,901 A | 4/1998 | Maumy et al. | |

FOREIGN PATENT DOCUMENTS

| | | | |
|---|---|---|---|
| DE | 2558446 | * 12/1976 | ................. 623/22 |
| EP | 0297789 | * 1/1989 | ................. 623/22 |
| EP | 0358600 | * 3/1990 | ................. 623/22 |
| EP | 0453694 | * 10/1991 | ................. 623/22 |
| EP | 046019 | * 12/1991 | ................. 623/22 |
| EP | 0 958 797 A1 | 11/1999 | |
| FR | 2 628 967 A1 | 9/1989 | |
| GB | 2126096 | * 3/1984 | ................. 623/22 |
| JP | 406285098 | * 10/1994 | ................. 623/22 |
| SU | 1676617 | * 9/1991 | ................. 623/22 |
| WO | WO 95/22944 | 8/1995 | |

* cited by examiner

*Primary Examiner*—David J. Isabella
(74) *Attorney, Agent, or Firm*—Morgan & Finnegan LLP

(57) ABSTRACT

A modular acetabular bearing assembly which minimizes or eliminates the production of wear debris resulting from relative motion at the interface between the acetabular shell and bearing insert portions of the modular acetabular bearing assembly. The modular acetabular bearing assembly includes an acetabular shell and composite bearing insert. The composite bearing insert includes an endoskeleton and a polymer layer which is preferably molded into and locked within the endoskeleton. The endoskeleton is configured to be locked within the acetabular shell. As such, the modular acetabular bearing assembly, and its method of manufacture, eliminate all contact between any polymer surface on the composite bearing insert and any metal surface on the acetabular shell. The modularity of the assembly facilitates the interchangeability of various composite bearing inserts within an acetabular shell which is fixed to the acetabulum of a patient. This provides for various advantages, including the ability to use a central screw to fix the acetabular shell to a patient.

6 Claims, 4 Drawing Sheets

ACETABULAR BEARING ASSEMBLY FOR TOTAL HIP JOINTS

FIELD OF THE INVENTION

The present invention relates generally to medical devices and, more particularly, to an acetabular bearing assembly of a total hip joint prosthesis for minimizing or eliminating the production of wear debris resulting from relative motion at the interface between the acetabular shell and polymer bearing insert portions of a modular acetabular bearing assembly.

BACKGROUND OF THE INVENTION

Hip surgery for the replacement and repair of hip joints has become relatively commonplace in recent years. Prosthetic hip joint devices are available from a variety of manufacturers. Such hip prosthetic systems, when properly installed, approximate a patient's natural hip movement.

Typical hip joint prostheses contain a femoral component and an acetabular component. The femoral component has an intramedullary portion which is fixed to the femur of a patient. The femoral component also has an attached ball portion which allows articulation, restricts dislocation or subluxation, and transfers loads to the acetabular component. The acetabular component may be unitary, including a concave bearing surface to articulate with the ball, and a fixation surface for attachment to the acetabulum. Acetabular components may be of modular construction, including a bearing insert portion and an acetabular shell portion which receives the bearing insert and is affixed to the acetabulum of a patient.

Currently available modular acetabular components use a polymeric material for the bearing insert. Such currently available modular acetabular components suffer from a tendency toward relative motion between the bearing insert and the acetabular shell portion. Such relative motion can cause wear and the generation of small particles from the polymeric bearing insert. Such wear can lead to failure of the hip joint prosthesis and lysis of the surrounding bone.

Various attempts to solve this problem include elaborate and often costly locking systems to minimize relative motion at the interface between the bearing insert and the metal acetabular shell portion. In addition, such attempts at solving this problem have often not been modular and therefore have lost the advantages of modularity, including the possibility of using screws to fix the metal acetabular shell portion to the acetabulum.

Accordingly, there is a need for a modular acetabular bearing assembly which either minimizes or eliminates the production of wear debris resulting from relative motion at the interface between the polymer bearing insert and metal acetabular shell portions of hip joint prostheses.

SUMMARY OF THE INVENTION

The present invention fulfills the aforementioned need by providing an acetabular bearing assembly for a total hip joint which either minimizes or eliminates the production of wear debris that results from relative motion at the interface between the polymer bearing insert portion and metal acetabular shell portions of a total hip joint prosthesis.

In one embodiment of the present invention, an acetabular bearing assembly is provided, which includes (1) an acetabular shell having an outer convex surface for fixation to a surgically prepared acetabulum and an inner concave surface, and (2) a composite bearing insert having a polymer layer and a metal layer, wherein the polymer layer forms a concave bearing surface shaped to receive a ball-end of a stem, and wherein the metal layer forms a convex surface to interlock with the concave surface of the acetabular shell. The composite bearing insert is constructed so that the metal layer and the polymer layer are interlocked to minimize relative movement therebetween. The acetabular bearing assembly may be configured such that the composite bearing insert contacts the acetabular shell only through metal-to-metal contact. In one embodiment of the invention, the composite bearing insert and metal acetabular shell are interlocked through a plurality of interlocking dovetails. In various other embodiments of the invention, the acetabular shell and composite bearing insert are interlocked through a locking arrangement selected from the group consisting of: a locking taper, a screw fastener, a pin fastener, a locking bayonet and a snap ring.

The present invention also includes a technique for constructing acetabular bearing assemblies. In one embodiment of the present invention, the method includes (1) constructing a metal layer in the form of a metal endoskeleton with a first locking mechanism and a second locking mechanism, wherein the first locking mechanism is disclosed on a concave portion of the metal endoskeleton and the second locking mechanism is supplied on a convex portion of the metal endoskeleton, (2) filling at least a portion of the metal endoskeleton with a polymeric powder, (3) molding the polymeric powder upon and within the metal endoskeleton to form and lock the polymeric bearing layer to the metal endoskeleton, and (4) locking the metal endoskeleton to an acetabular shell. In various embodiments of the invention, the locking mechanisms between the endoskeleton and the acetabular shell may include a locking taper or threaded surface.

The details of the various embodiments of the present invention are set forth in the accompanying drawings and description below. Numerous additional features and advantages will become apparent from a review of the following details of various embodiments of the present invention.

DETAILED DESCRIPTION OF VARIOUS EMBODIMENTS OF THE PRESENT INVENTION

Figure 1:
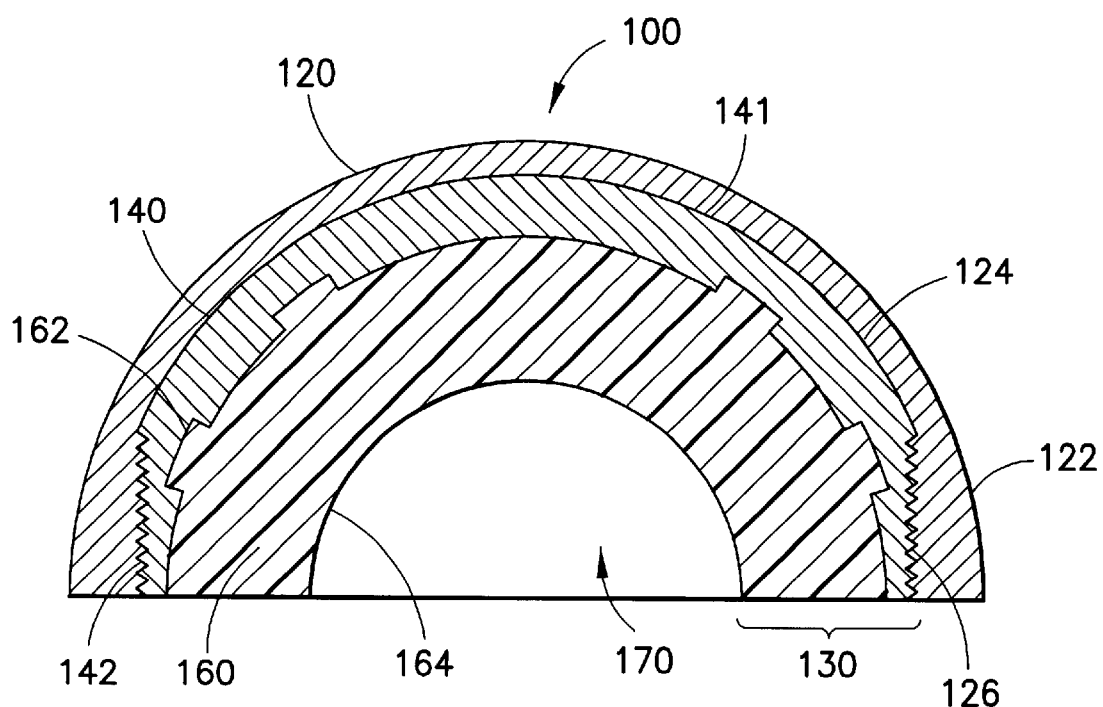
FIG. 1 is a cross-sectional view of an acetabular bearing assembly for total hip joints in accordance with one embodiment of the present invention.

With reference to the drawings, various embodiments of the present invention will now be shown and described. The leading numeral of each reference numeral indicate the first drawing in which that reference numeral is introduced. The trailing two numerals of each reference number are consistently used throughout the drawings to designate counterpart or like elements.

With reference to FIG. 1, a cross-sectional view of an acetabular bearing assembly in accordance with one embodiment of the present invention is shown. In general, the acetabular bearing assembly 100 of the present invention consists of two elements: an acetabular shell portion 120 and a composite bearing insert 130, each of which will now be described in greater detail below.

The acetabular shell portion 120 is preferably made of a suitable, bio-compatible material that allows the outer convex surface 122 to be fixed to a surgically-prepared acetabulum. The acetabular shell 120 may be fixed to the acetabulum by various techniques including biological fixation, mechanical fixation, or grouting fixation. The acetabular shell 120 has an inner concave surface 124 configured to receive the composite bearing insert 130 therewithin. The acetabular shell 120 of the embodiment of FIG. 1 further includes a threaded portion 126 to lock the acetabular shell 120 to the composite bearing insert 130.

The acetabular shell 120 may be made of biocompatible metal, such as titanium or titanium alloy, cobalt-chrome alloy, or a suitable low corrosion iron alloy. In the alternative, the acetabular shell 120 may be made of ceramic, or a composite material of suitable strength and stiffness.

The second component of the acetabular bearing assembly 100 is a composite bearing insert 130 made of the endoskeleton 140 and the polymer layer 160. As such, the bearing insert is a composite structure of a polymer and a stiffer, stronger material such as a bio-compatible metal, including titanium or titanium alloy, cobalt-chrome alloy or a suitable low corrosion iron alloy. The polymer layer 160 forms a concave bearing surface 164 which receives the ball-end of a stem in the cavity 170. The endoskeleton 140 of the composite bearing insert 130 is received by, and locked into, the concave surface 124 of the acetabular shell portion 120.

In one embodiment of the present invention, the polymer layer 160 is attached to the endoskeleton 140 by means of an interlocking structure such as dovetails or tapered holes 162. In the alternative, mechanical, chemical or adhesive bonding may be used to interlock the endoskeleton 140 and the polymer layer 160. This interlocking structure eliminates meaningful relative motion between the two portions of the composite bearing insert, thus minimizing or eliminating the production of wear debris that results from relative motion at the interface between the endoskeleton 140 and the polymer layer 160.

The endoskeleton 140 of the composite bearing insert is received by, and locked into, the concave surface 124 of the acetabular shell portion 120. Preferably, the composite bearing insert 130 may be shaped so that its outer convex surface 141 contacts the inner concave surface 124 of the acetabular shell 120 only by metal-to-metal contact. As such, the present invention minimizes the generation of wear debris by eliminating contact between any polymer surface on the composite bearing insert 130 and any metal surface on the acetabular shell 120. In addition, the shell/endoskeleton interface may be configured to have on the non-tapered portion of the interface an appropriate small clearance between the acetabular shell 120 and endoskeleton 140 along curved portions of the shell 120 and endoskeleton 140.

The present invention further provides a suitable locking mechanism between the composite bearing insert 130 and the acetabular shell 120. This may be accomplished through a number of techniques including screws or pin fasteners, locking bayonets, taper locking surfaces or snap rings. With reference to FIG. 1, the threaded portion 126 of the acetabular shell 120 and the threaded portion 142 of the endoskeleton 140 form a threaded interface to interlock the composite bearing insert 130 and the acetabular shell 120. The threaded interface may be further treated with a polymer locking surface and augmented by locking pins to prevent back out of the threads.

Figure 2:
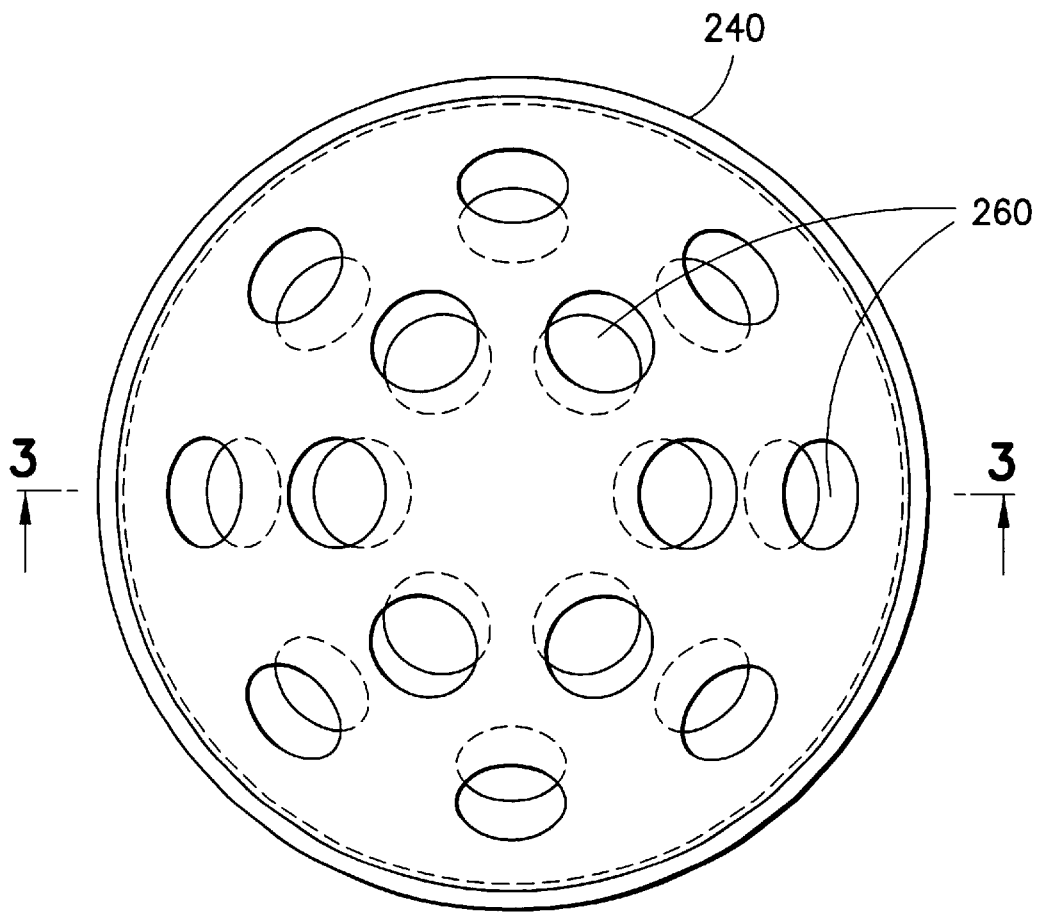
FIG. 2 is a top view of a metal endoskeleton having a plurality of radial blind dovetail dovetail holes in accordance with another embodiment of the present invention.
Figure 3:
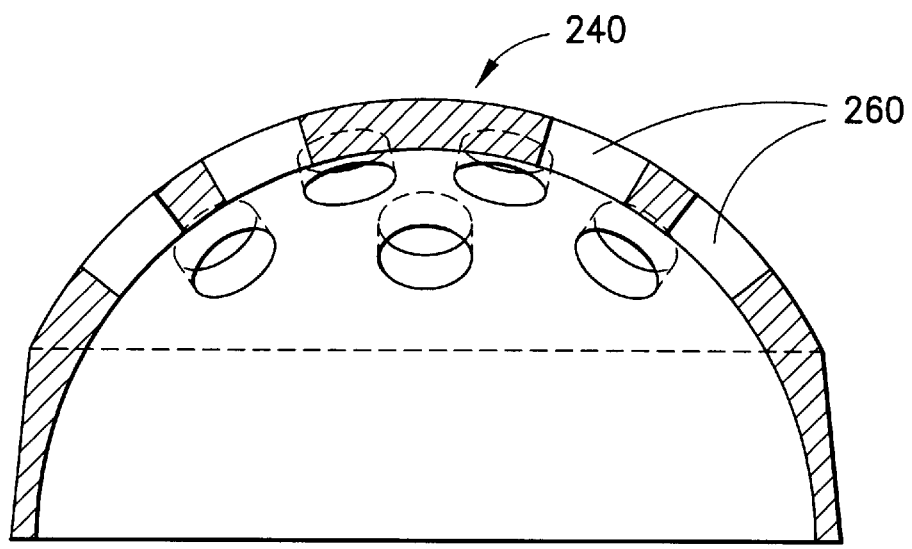
FIG. 3 is a cross-section of the endoskeleton shell of FIG. 2 along lines 3—3.

With reference to FIGS. 2 and 3, an alternate embodiment of the endoskeleton 240 is shown. The endoskeleton 240 has a plurality of blind radial dovetail holes 260. These radial tapered holes 260 may extend through the endoskeleton 240. As such, a polymer layer may be molded within the endoskeleton 240 such that the polymer extends into holes 260, thereby locking the polymer bearing layer to the endoskeleton 240.

Figure 4:
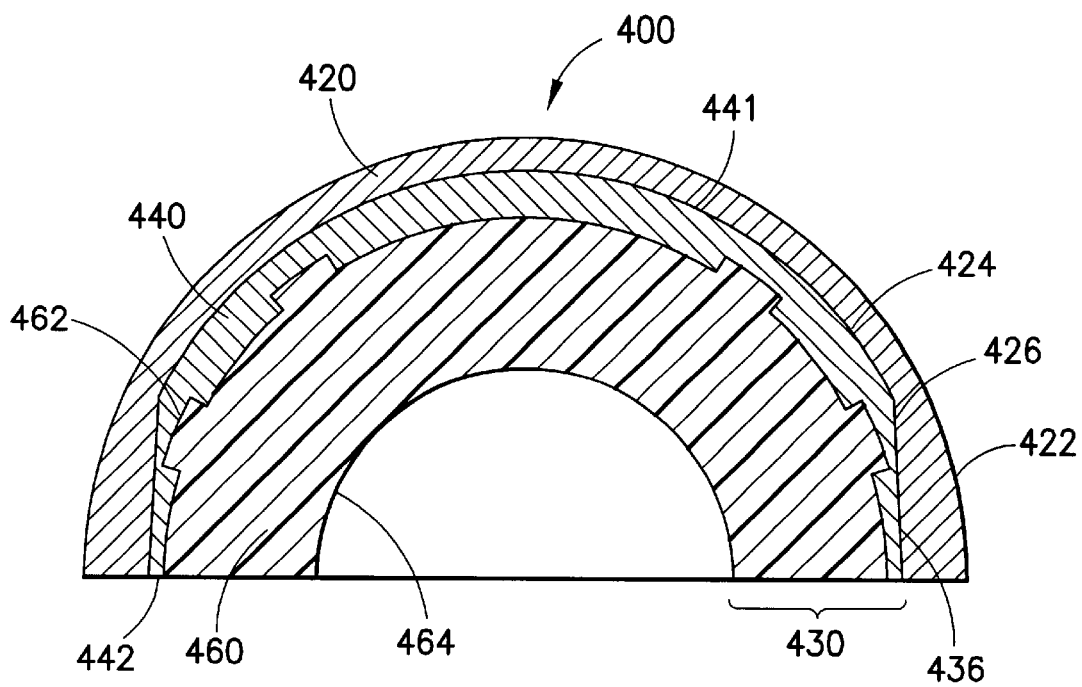
FIG. 4 is a cross-sectional view of an alternate embodiment of a composite bearing assembly in accordance with another embodiment of the present invention.

With reference to FIG. 4, an acetabular bearing assembly 400 may include an acetabular shell 420 which is interconnected to the composite bearing insert 430 through a locking or morse taper 436. The locking taper 436 includes a taper element 426 on the concave side 424 of the acetabular shell portion 420 and a taper element 442 on the convex surface 441 of the endoskeletal portion 440. Such a tapered locking mechanism offers the advantages of an unlimited number of positions of rotational engagement, while transmitting both axial and torsion loads with minimum relative motion at the locking interfaces. The remaining elements of the embodiment of FIG. 4 are similar to the corresponding elements of the embodiment of FIG. 1: a convex outer surface 422, a polymer bearing layer 460, several dovetails 462 and a bearing surface 464.

Figure 5:
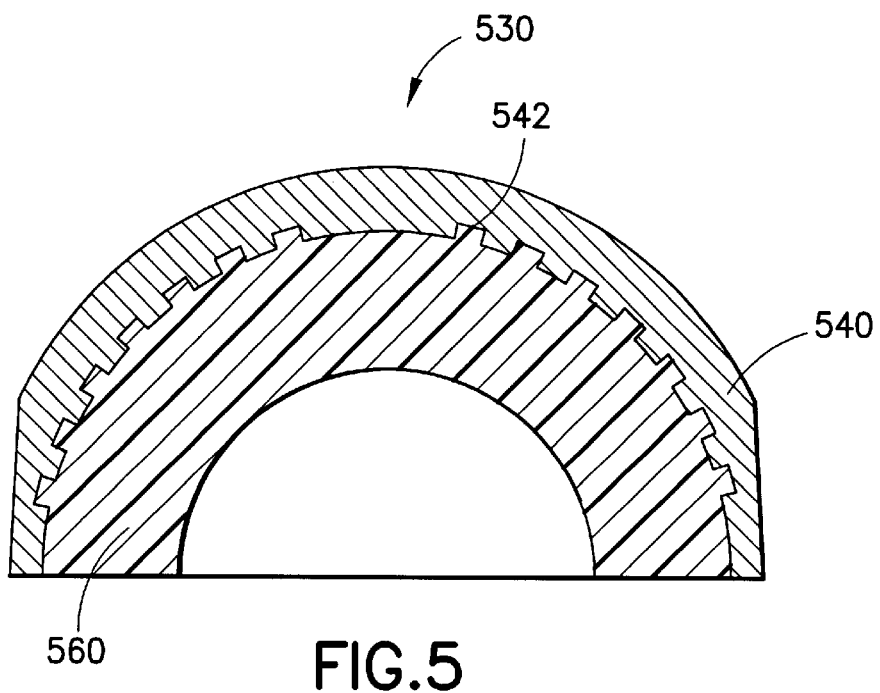
FIG. 5 is a cross-sectional view of a composite bearing insert in accordance with another embodiment of the present invention.

With reference to FIG. 5, another embodiment to the present invention is shown. The composite bearing insert 530 contains an interlocking interface formed between the endoskeleton 540 and the polymer bearing layer 560. In this embodiment, the endoskeleton 540 includes several undercuts or stump projections 562 which project into the polymer layer 560. As such, the endoskeleton 540 includes a beaded surface containing the undercuts or stump projections 562.

Figure 6:
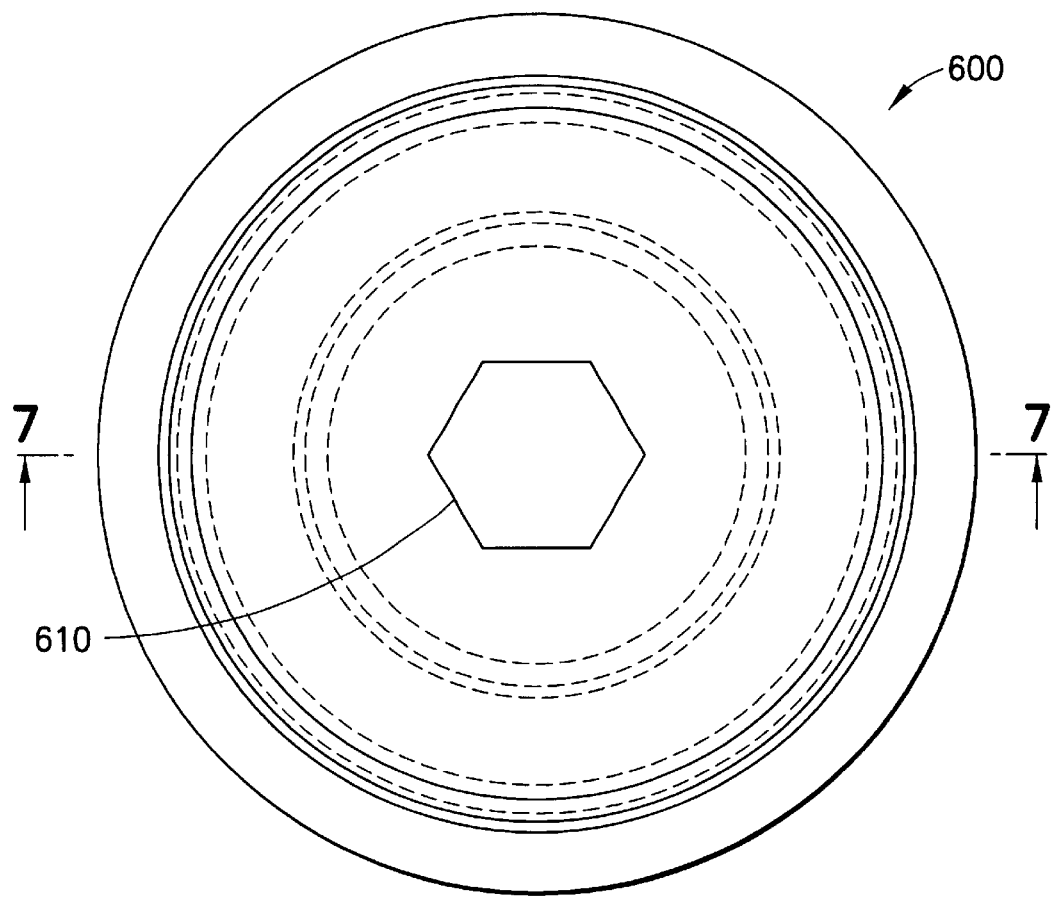
FIG. 6 is a top view of an alternate embodiment of an acetabular bearing assembly in accordance with another embodiment of the present invention.
Figure 7:
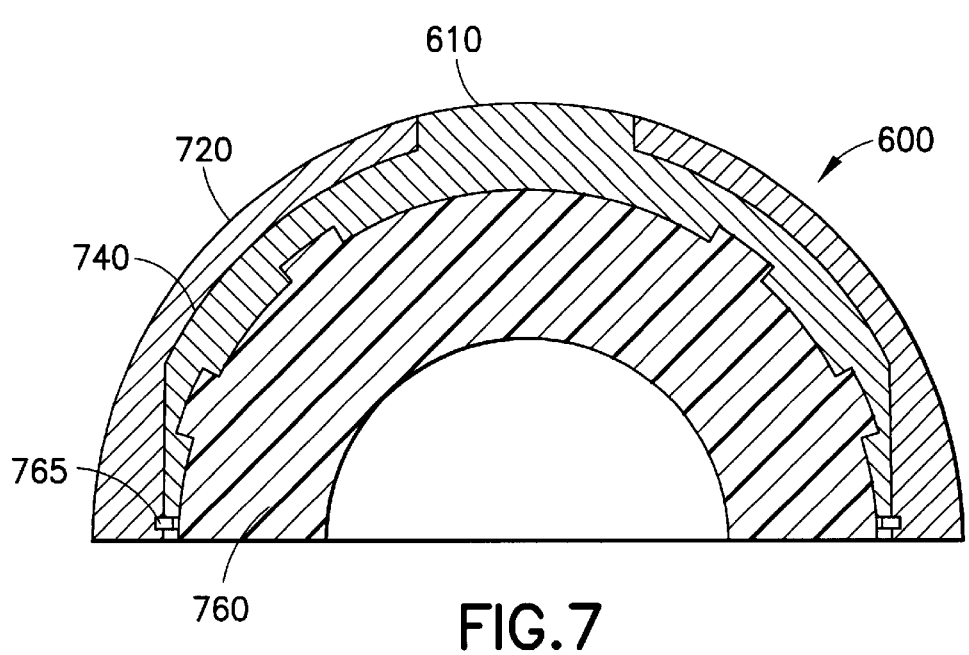
FIG. 7 is a cross-sectional view of the embodiment to FIG. 6 along lines 7—7.

With reference to FIGS. 6 and 7, another embodiment to the present invention is shown in which a multifaceted structure 610 is used to prevent rotation between the acetabular shell 720 and endoskeleton 740. Although a hexagonal shape 610 is shown, it is to be understood that other polygonal shapes or an oval shape may be used to prevent relative rotation between the acetabular shell 720 and the endoskeleton 740.

In the embodiment of FIGS. 6 and 7, the acetabular shell 720 and endoskeleton 740 may be configured so that a portion of the shell/endoskeleton interface is spherical. In addition, a snap ring locking device 765 may be used to interlock the endoskeleton 740 and acetabular shell 720. Moreover, the polymer bearing layer 760 may have a plurality of lip extensions over the edge or face of the endoskeleton or acetabular shell to provide an asymmetric face.

The remaining elements of this acetabular bearing assembly 600 may be similar to the structures found in the embodiments of FIGS. 1–5.

Method of Manufacture

In manufacturing the composite bearing insert element of the present invention, one method includes attaching the polymer bearing layer of the insert to the metal endoskeleton by molding, such as by compression molding. Preferably, the polymer material used is ultra-high molecular weight polyethylene.

In implementing this method, the metal endoskeleton portion of the composite bearing insert may be suitably shaped or surfaced to securely interlock with, or bond to, the polymer bearing layer. As previously discussed, one locking technique involves providing wedge-shaped mating surfaces at the endoskeleton/polymer layer junction so as to mechanically lock the two portions by the action of the shrinking of the polymer about the endoskeleton at the time of molding. This locking technique could involve the formation of dovetails, such as the dovetails 162 shown in FIG. 1. Another technique would involve the formation of tapered holes in the endoskeleton, such as the tapered holes 260 shown in FIGS. 2 and 3. These techniques effectively interlock the endoskeleton and polymer bearing layer, thereby preventing relative movement therebetween. Locking of the polymer layer to the endoskeleton may also be accomplished by coating the concave surface of the endoskeleton with a beaded metal layer, a coated undercut surface layer produced by plasma spraying or electrical surface undercutting.

By the aforementioned detailed description and the attached drawings, a number of embodiments of the present invention have been shown and described. It is to be understood that various modifications may be made without departing from the spirit and scope of the invention. Accordingly, it is to be understood that the invention is not to be limited by the illustrated and described embodiments, but by the scope of the appended claims.

What is claimed is:

1. A method of constructing an acetabular bearing assembly comprising:

constructing a metal endoskeleton with a first locking mechanism and a second locking mechanism, said first locking mechanism disposed on a concave portion of said metal endoskeleton and said second locking mechanism supplied on a convex portion of said metal endoskeleton;

filling at least a portion of said metal endoskeleton with polyethylene powder; and molding said polyethylene powder within said metal endoskeleton to form and lock a polyethylene layer within said metal endoskeleton.

2. The method of claim 1 further comprising locking said metal endoskeleton to an acetabular shell.

3. The method of claim 1 wherein said first locking mechanism is selected from the group consisting of a plurality of interlocking dovetails, beaded surfaces, undercut surfaces, and chemically bonding surfaces.

4. The method of claim 1 wherein said second locking mechanism is selected from the group consisting of an external thread and a locking taper.

5. A method of constructing an acetabular bearing assembly comprising:

constructing a metal endoskeleton with at least one tapered hole extending at least partly though said metal endoskeleton;

filling at least a portion of said metal endoskeleton with polyethylene powder such that said polyethylene powder fills at least a portion of said tapered hole; and molding said polyethylene powder within said metal endoskeleton and said tapered hole to form and lock a polyethylene layer within said metal endoskeleton.

6. The method of claim 5 wherein said tapered hole extends through said metal endoskeleton.

* * * * *